United States Patent
Suson

(10) Patent No.: US 6,508,779 B1
(45) Date of Patent: *Jan. 21, 2003

(54) ADJUSTABLE FLOW RATE GLAUCOMA SHUNT AND METHOD OF USING SAME

(76) Inventor: John Suson, 362F Willow Grove Dr., Pewaukee, WI (US) 53072

(*) Notice: Subject to any disclaimer, the term of this patent is extended or adjusted under 35 U.S.C. 154(b) by 0 days.

This patent is subject to a terminal disclaimer.

(21) Appl. No.: 08/788,940

(22) Filed: Jan. 24, 1997

Related U.S. Application Data

(63) Continuation of application No. 08/435,037, filed on May 5, 1995, now Pat. No. 5,626,558.

(51) Int. Cl.⁷ .................................................. A61M 5/00
(52) U.S. Cl. ........................................... 604/8; 604/294
(58) Field of Search ................................ 604/8–9, 289, 604/294

(56) References Cited

U.S. PATENT DOCUMENTS

| | | |
|---|---|---|
| 3,788,327 A | 1/1974 | Donowitz et al. |
| 3,915,172 A | 10/1975 | Wichterle et al. |
| 4,037,604 A | 7/1977 | Newkirk |
| 4,402,681 A | 9/1983 | Haas et al. |
| 4,428,746 A | 1/1984 | Mendez |
| 4,457,757 A | 7/1984 | Molteno |
| 4,521,210 A | 6/1985 | Wong |
| 4,554,918 A | 11/1985 | White |
| 4,604,087 A | 8/1986 | Joseph |
| 4,722,724 A | 2/1988 | Schocket |
| 4,750,901 A | 6/1988 | Molteno |
| 4,826,478 A | 5/1989 | Schocket |
| 4,886,488 A | 12/1989 | White |
| 4,936,825 A | 6/1990 | Ungerleider |
| 4,946,436 A | 8/1990 | Smith |
| 5,000,731 A | 3/1991 | Wong et al. |
| 5,092,837 A | 3/1992 | Ritch et al. |
| 5,171,270 A | * 12/1992 | Herrick ...................... 623/11 |
| 5,178,604 A | 1/1993 | Baerveldt et al. |
| 5,300,020 A | 4/1994 | L'Esperance, Jr. |
| 5,338,291 A | * 8/1994 | Speckman et al. ............. 604/8 |
| 5,346,464 A | 9/1994 | Camras |
| 5,433,701 A | 7/1995 | Rubinstein |
| 5,486,165 A | * 1/1996 | Stegmann ................... 604/294 |

* cited by examiner

*Primary Examiner*—Dennis Ruhl
(74) *Attorney, Agent, or Firm*—Foley & Lardner

(57) ABSTRACT

An adjustable flow rate implantable shunt device for use in treating glaucoma is provided. The device comprises a tubular member having a first sealed end and an open second end which are joined by a wall. The first end is inserted into the anterior portion of the eye for receipt of aqueous humor, and the second end is fastened to the sclera of the eye. The first end of the shunt device is sealed when implanted, so that flow of aqueous humor through the device immediately after implantation is prevented. After a sufficient post-implantation period such that a fibrous capsule has formed around the shunt device, at least one perforation is made along the segment of the wall of the tubular member which is located within the anterior portion of the eye to allow aqueous humor to flow through and out of the device.

4 Claims, 2 Drawing Sheets

ADJUSTABLE FLOW RATE GLAUCOMA SHUNT AND METHOD OF USING SAME

This is a continuation of application Ser. No. 08/435,037 filed on May 5, 1995, now U.S. Pat. No. 5,626,558.

BACKGROUND OF THE INVENTION

This invention relates generally to the drainage of aqueous humor from an eye to relieve the elevated pressure characteristic of glaucoma. More specifically, the present invention relates to an implantable glaucoma shunt device and related method, which prevents or limits drainage of aqueous humor from the eye initially after implant to avoid damage to the eye, and additionally allows the rate of flow of aqueous humor from the device to be initiated or adjusted periodically after implantation.

Aqueous humor is continuously produced by the ciliary body in the posterior chamber of the eye, and from there it flows through the pupil into the anterior chamber of the eye. In order to maintain relatively constant intraocular pressure, aqueous humor must be drained away continuously. It passes primarily through the trabecular meshwork of the anterior chamber and into the canal of Schlemm, before draining into the veins leaving the eye.

Normal intraocular pressure is typically about 15+/−4 mm Hg, but may rise to 21 mm Hg. Pressures within the eye that are substantially above this range are considered abnormally high. Chronically elevated intraocular pressure (resulting, for example, from a defect in intraocular drainage) can give rise to glaucoma. Glaucoma can cause irreversible damage to certain structures of the eye, including the optic nerve, and is a leading cause of blindness in the United States.

There are many types and causes of glaucoma. Treatment of the disease depends on both the patient and the form of glaucoma. As a rule, the damage caused by glaucoma can not be reversed. The goal, therefore, of glaucoma treatment is to prevent further damage and to preserve existing vision.

Glaucoma can often be controlled with medical therapy, typically through topical medications, such as pilocarpine, timolol maleate, betaxolol, or epinephrine, and also through systemic medications, including acetazolamide. Medical therapy either decreases the rate of production of aqueous humor, or increases its outflow from the anterior chamber. However, with many patients these procedures are not effective because the patients fail to follow the treatment prescribed, due to either negligence or the relatively high cost of the medication. Other potential problems with medical treatment include side effects and inadequate control of the intraocular pressure.

If the maximum-tolerated dose of medication fails to control the intraocular pressure, then laser trabeculoplasty or filtering surgery to increase aqueous drainage is usually indicated. These procedures seek to increase the rate of outflow of aqueous humor. Other types of surgical procedures seek to reduce the formation of aqueous humor, by destroying the tissue where it is created. These procedures are typically indicated only after filtering surgery has failed. If such filtering surgery has failed to control the intraocular pressure, or if the patient has a poor prognosis for filtering surgery, implantation of a glaucoma shunt may be indicated.

Glaucoma shunts typically drain aqueous humor from the anterior chamber of the eye to the fibrous capsule (bleb) which forms around a collecting device placed on the posterior portion of the globe of the eye, and the humor is then reabsorbed into the vascular system. The bleb is formed apparently due to an immune response against the shunt, which the host recognizes as a foreign body. Bleb formation is essential for a successful implant procedure and recovery by the patient.

Glaucoma shunts typically consist of a silicone elastomer catheter which is inserted into the anterior chamber, and which connects to an episcleral plate or an encircling band. Episcleral plates are commonly made of silicone elastomer, polypropylene or acrylic materials.

Glaucoma shunt implantation is subject to a number of complications. In the early post-implantation period, excessive drainage of aqueous humor from the anterior chamber can cause low intraocular pressure (hypotony), resulting in shallow anterior chamber depth. This can lead to choroidal detachment, hemorrhage or hypotony maculopathy. The hypotony is typically alleviated as the fibrous capsule forms around the posterior plate or encircling band. In the long-term, excess fibrous tissue can obstruct the flow of aqueous humor from the shunt through the bleb and into the vascular system. This causes an increase in the intraocular pressure and results in clinical failure of the device. The shunts known in the art typically have had some ligature or plug which was removable or biodegradable, to prevent flow of aqueous humor through the device for an initial period after implantation, allowing sufficient time for the bleb to form before drainage begins. Further, if the flow rate from the shunt is too low, insufficient amounts of aqueous humor may be drained from the eye. Such drainage may be insufficient to lower intraocular pressure to a degree which will prevent further damage from glaucoma.

Prior art shunt devices had attempted to adjust the flow rate of aqueous humor from the device by varying the radius of the shunt tube. However, the rate of flow (f) of aqueous humor through a tube is proportional to the radius (r) of the shunt tube to the fourth power (f $r^4$). Therefore, attempts to a adjust the flow rate by changing the radius of the shunt tube were not practical due to the inability to make precise adjustments. For example, changing the radius of the shunt tube from 2 mm to 3 mm resulted in an increase of flow rate from 16 to 81. Therefore, a shunt device that allows the flow rate of aqueous humor to be adjusted in a linear fashion, which would allow precise and accurate adjustments to be made in the flow rate of aqueous humor, would be desirable.

In order to adequately relieve intraocular pressure, it is advantageous for an implant device to meet three requirements: (1) the device must be able to block most or all of the flow of aqueous humor through the device for the initial period after implantation until the bleb has formed about the device; (2) the device must be able to prevent collapse of the eye after the flow of aqueous humor through the device is increased to a level sufficient to relieve intraocular pressure; and (3) the device must allow aqueous humor to drain from the eye at a sufficient rate to successfully treat the glaucomatous condition. Prior art shunt devices to prevent excess flow of aqueous humor from the device utilized complicated systems of pressure sensitive slit valves, check valves or photosensitive polymers.

Accordingly, there has been a need for a novel glaucoma shunt which, in the immediate post-implantation period, can provide resistance to flow to prevent hypotony and its complications until the fibrous capsule forms around the end of the shunt from which the aqueous humor drains, to prevent damage to the eye. Additionally, such a shunt should be capable of having its flow rate initiated or increased, and thereafter adjusted incrementally in a quick and easy fashion, after implantation by the physician. Further a glaucoma shunt is needed which accomplishes its desired function and is easy to manufacture and use, and which provides a desirable shunting function reliably over an extended period of time. The present invention fulfills these needs and provides other related advantages.

SUMMARY OF THE INVENTION

The present invention resides in an improved glaucoma drainage device and in a method of using the device for shunting excess aqueous humor from the eye. The device and methods of the invention allow for periodic post-implantation linear adjustment of the flow rate of aqueous humor from the anterior portion of the eye through the device to the outside of the eye.

More specifically, the glaucoma drainage device comprises a hollow tubular member having first and second ends, with the first end being sealed and the second end being open and joined to the first end by a wall, and comprising a material which may preferably be perforated by a low power laser after implantation of the device. The glaucoma drainage device may further comprise a plate attached to the second end. This plate would allow easier attachment of the device to the eye during implantation and also facilitate in the adequate formation of a bleb while preventing excessive fibrosis around the second end.

Further, the wall of the tubular member may contain preformed depressions over various segments along the wall's length which may exist as scalloped sections or grooves along the length of the wall, wherein the wall at these segments is thinner than at the remaining segments of the wall. These depressions are located in the portion of the wall of the tubular member situated in the anterior portion of the eye after implantation, allowing perforation of the tube at these points with less laser energy (e.g., from a lower powered laser) than would be required for the remaining thicker segments of the wall. By perforating the tubular member rather than varying the radius of the tubular member, the flow rate of aqueous humor through the device can be modified in a precise, regulated linear fashion.

Additionally, the wall of the tubular member may have one or more openings prior to implantation, to allow aqueous humor to drain through and from the device immediately after implantation, at a flow rate low enough to prevent the dangers resulting from a rapid post-implantation decrease in intraocular pressure, but inadequate to lower intraocular pressure sufficiently to prevent damage associated with glaucoma. These initial openings are located within the portion of the tubular member residing in the anterior portion of the eye after implantation. This initial flow rate can then be increased to allow adequate flow of aqueous humor from the device to treat the glaucomatous eye (i.e., prevent damage associated with glaucoma and associated excess pressure), by the creation of one or more openings or perforations (holes) within the portion of the wall of the tubular member located within the anterior chamber of the eye after implantation as previously described. The flow rate can be adjusted in a linear fashion periodically as required by the attending physician, in order to increase the flow rate of aqueous humor in a precise manner and thereby lower intraocular pressure, by the simple method of placing additional perforations within wall of the tubular member. The perforations or openings in the wall of the tubular member are preferably and conveniently made using a laser.

In an alternative embodiment of the invention, the glaucoma drainage device comprises a hollow tubular member, having a first end and a second end, wherein the second end is ensconced in a sealed reservoir. The first end of the tubular member is inserted into the anterior chamber of the eye, and the reservoir in which the second end is ensconced may be located outside the eye on top of the sclera. The flow rate of aqueous humor through the device may be initiated and thereafter periodically adjusted in a linear manner at any time after implantation in order to increase the flow rate of aqueous humor and thereby lower intraocular pressure, by placing one or more openings or perforations in the reservoir. If the reservoir is located outside of the eye, the openings or perforations may be created by non-mechanical means such as a laser. Additionally, one or more openings or perforations may be placed in the reservoir prior to implantation, allowing a small rate of flow of aqueous humor from the device, but at a low level which is insufficient to relieve all of the intraocular pressure due to glaucoma.

It is also an object of the invention to provide a method for treating glaucoma comprising the insertion of an adjustable flow rate drainage device of the invention into the anterior chamber of the eye to allow linear adjustment of intraocular pressure.

More specifically, the method for treating glaucoma with an implanted shunt of the invention includes the steps of inserting the first sealed end of the tubular member into the anterior chamber of the eye, and securing the second open end of the tubular member to the sclera of the eye. The second open end may have a plate secured to it; the plate thereby being fastened to the sclera of the eye. Initial post-implantation flow of aqueous humor through the device may be prohibited, or alternatively, may be allowed at a minimal rate until the point in time that an increased flow rate could be safely initiated without endangering the patient. This initial flow rate would take place from one or more openings or perforations within the portion of the wall of the tubular member located within the anterior chamber of the eye and would allow a small amount of drainage of aqueous humor, at a rate that would not be dangerous to the eye, but would not be sufficient to alleviate the intraocular pressure due to glaucoma within the eye. A sufficient post-implantation period of time is allowed to pass and the physician may thereafter place small openings or perforations in the portion of the portion of the wall of the tubular member located within the anterior chamber, whereby the flow of aqueous humor from the anterior chamber of the eye into the tubular member and flow out of the tubular member is initiated or increased linearly to a rate sufficient to treat the glaucomatous eye, depending on whether the device was initially sealed, and the excess aqueous humor will be reabsorbed into the vascular system. The initial opening(s) in the wall of the tubular member could be made prior to implantation, or may be created after implantation. The glaucomatous condition can thereafter be monitored by the physician, and if intraocular pressure increases, additional openings or perforations may be placed within the portion of the wall of the tubular member located within the anterior chamber of the eye to increase the flow rate of aqueous humor from the eye, through the device. Additional perforations may be created in this portion of the wall of the tubular member at any time after implantation to increase the flow of aqueous humor. These perforations may be made by a laser, which is directed through the cornea of the eye to the tubular member. A low watt laser is used so as to avoid damage to the eye. This procedure of creating additional perforations to adjust the flow rate of aqueous humor from the device may be done on an out-patient basis.

Accordingly, it is an object of the present invention to provide a device or apparatus for implant in or at the eye, and a method to treat glaucoma by reducing intraocular pressure in the anterior chamber in stages, by allowing little or no aqueous humor to drain from the eye through the implant during the initial post-implantation period, and thereafter allowing the flow rate of aqueous humor through the device to be adjusted in a linear fashion easily, quickly, precisely and relatively painlessly at various post-implant time periods, as required.

DETAILED DESCRIPTION OF THE PREFERRED EMBODIMENT

Figure 1:
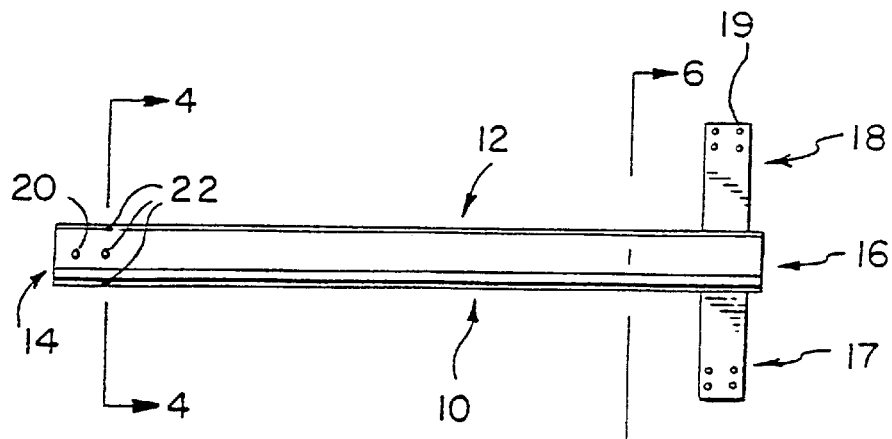
FIG. 1 is a top plan view of a glaucoma shunt which embodies the teachings of the present invention.
Figure 2:
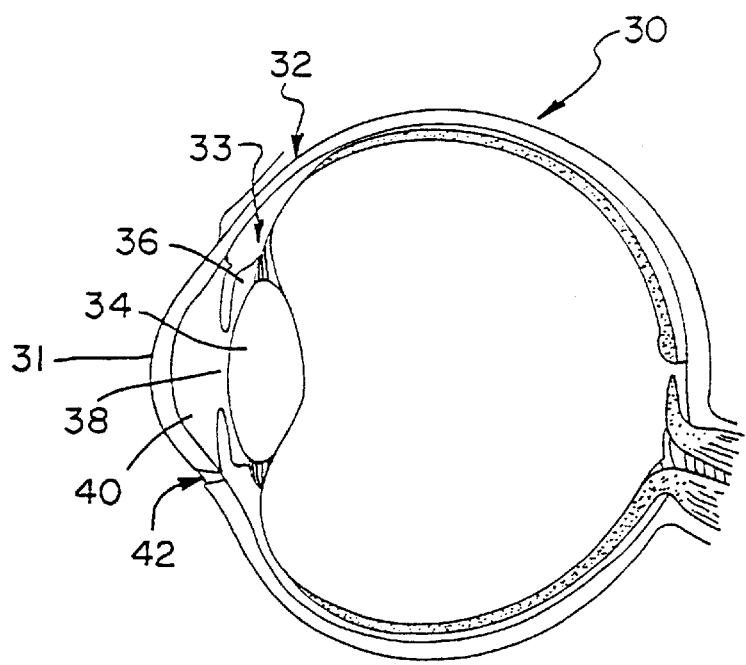
FIG. 2 is a sectional view of an eye.
Figure 6:
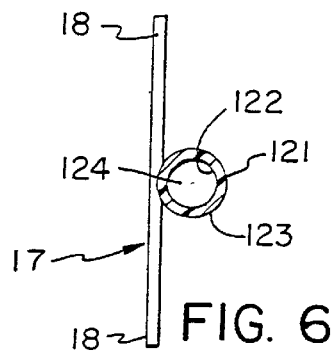
FIG. 6 is a cross view of the shunt shown in FIG. 1 of the tubular member 12 of a shunt 10 of the invention.

As shown in FIG. 1 for the purpose of illustration, the present invention is concerned with an improved, adjustable flow-rate glaucoma shunt device, designated by the reference number 10. The improved glaucoma shunt 10 comprises a hollow tubular member 12 having a first sealed end 14 and a second open end 16, which are joined by the wall 121 of the tubular member 12, as most clearly seen in FIGS. 1 and 6. Tubular member 12 also has an inside surface 122 and an outside surface 123 illustrated in FIG. 6. Aqueous humor passes through bore 124 of tubular member 12. Second end 16 may optionally be attached to an episcleral plate 17. The episcleral plate 17 is attached to the second end 16 in any suitable manner, the preferred manner being suturing the plate directly to the second end. The episcleral plate may be molded to have a spherical arch shape which matches the arch shape of the posterior portion of the eye 30, as shown in FIG. 2. The plate 17 further comprises flanges 18. The flanges 18 have perforations 19 within flanges 18 which may be used by a physician to suture the plate 17 directly to the sclera 32 of the eye 30 for secure placement of the shunt 10 during the implantation, as further illustrated in FIG. 3.

Additionally, from prior to implantation, wall of the shunt 10 may optimally contain one or more initial perforations 20 in the tubular member 12 to allow a small amount of aqueous humor to drain from the eye immediately after implantation. The perforations 20 allow aqueous humor to drain at a low rate, allowing a moderate pressure release in the anterior chamber at a very restricted rate to assure against collapse of the anterior chamber or other damage to any other part of the eye at the time of implantation. Perforations 20 are located within the portion of the wall of the tubular member 12 located within the anterior chamber 40 of the eye 30. However, the perforations 20 are of insufficient size and/or quantity to allow the amount of aqueous humor draining to sufficiently lower intraocular pressure to treat glaucoma or otherwise provide the beneficial drainage required to treat the glaucomatous condition of the eye. Following implantation, a sufficient period of time, approximately two weeks, is allowed to elapse to allow the formation of a dense, fibrous capsule ("bleb") around the shunt 10. This bleb is shown as 44 in FIG. 3.

The present invention advantageously prohibits or severely restricts the flow of aqueous humor through the drainage shunt initially after implantation, but does not rely on complicated check valves, or biodegradable or removable components, to do so. Rather, the present invention utilizes a sealed glaucoma shunt, effectively prohibiting flow of aqueous humor from the shunt until such post-implantation time when a sufficient bleb has formed about the shunt. Alternatively, the glaucoma shunt is not initially sealed, but instead allows a severely restricted flow of aqueous humor through the device after implantation, to prevent damage to the eye which may result from rapid decrease in intraocular pressure that would occur if unrestricted flow through the device were allowed to occur at implantation. This initial restricted flow is insufficient to beneficially lower intraocular pressure to treat the glaucomatous condition, but may allow a small decrease in pressure sufficient during that period of time to prevent further damage to the eye while the bleb formation is occurring.

After formation of the bleb, additional perforations 22 are provided in the portion of the wall of tubular member 12 located within the anterior chamber 40 of the eye 30 to allow a sufficient flow of aqueous humor from the shunt 10 to allow a release of intraocular pressure that is sufficient to treat glaucoma (i.e., prevent continuing damage to the eye that would result from the high pressure of the aqueous humor that is present in the glaucomatous eye). The additional perforations allow the flow of aqueous humor to be increased in a precise linear fashion. The additional perforations 22 may be provided in a series of procedures, with one or more perforations being created each time. This may be done on an out-patient basis, with no need for costly and time-consuming hospital stays to create the additional perforations 22 in wall of tubular member 12 of the shunt 10. The perforations 22 may be provided in a number of sequential procedures, such that the flow rate of aqueous humor may adjusted linearly by increments as the situation warrants. Linear incremental adjustments in the flow rate of aqueous humor allow the physician to monitor the pressure inside the eye by standard procedures, and increase the rate of flow of aqueous humor in a precise fashion if required due to an increase in intraocular pressure. Further, by allowing a series of perforations to be produced, the present invention protects against the danger of blockage of release of aqueous humor from the device from occurring. Such blockage of one or more perforations may occur under a number of circumstances, including tissue growth. If one or more perforations become blocked, the physician may, if required, place additional perforations 22 within the portion of the wall of tubular member 12 located within the anterior chamber 40 of the eye 30 in one or more separate procedures, thus allowing the physician to effectually reopen the flow of aqueous humor from a blocked shunt 10, without requiring further invasive procedures.

Tubular member 12 and plate 17 are comprised of physiologically inert, resilient, nonbiologically degradable material such as polymethylmethacrylate, polypropylene, or silicone, with the preferred material being silicone. The material may be translucent or pigmented, the pigmentation allowing easier perforation of the material to be perforated by some types of lasers. The shunt 10 is designed to be an appropriate size to fit within the eye of a human. The tubular member 12 may have an inner diameter (ID) of bore 124 ranging from approximately 0.3–0.8 mm and wall thickness, between inside surface 122 and outside surface 123, of approximately 0.15–0.40 mm. In the preferred embodiment, the tubular member 12 is 0.5 mm ID and has a wall thickness of 0.2 mm and comprises or consists of silicone tubing. The length of tubular member 12, between end 14 and end 16, may range from approximately 10 mm to 30 mm, with a preferred length of 20 mm.

Perforations 20 are optionally created within and through the wall of tubular member 12 prior to implantation. The perforations 20 are created prior to implantation by any device capable of producing perforations of the proper dimension through the wall of tubular member 12, including nonmechanical means such as a laser. The preferred device for creating the perforations 20 and post-implantation perforations 22 is an argon or Nd;YAG laser, with the most v preferred being a Nd;YAG laser at a setting of 3–5 millijoules for 50–100 pulses. The perforations 20 and 22 in wall 121 of tubular member 12 should be of approximately 10 microns in diameter and are located in the portion of the wall of tubular member 12 located within the anterior chamber 40 of the eye 30. The size of the perforations 20 and 22 is critical for proper functioning of the shunt. If the perforations 20 and 22 have a diameter that is too small, fibrous tissue from the bleb will tend to invade the perforations 20 and cause them to clog and prevent flow of aqueous humor from the perforations 20 and 22. If the perforations 20 and 22 are larger than approximately 30–50 microns, it is likely that hypotony would result from a too rapid flow rate.

With reference to FIG. 2, the eye 30 will be explained in suitable detail so as to allow an understanding of the method for implanting the device of the present invention. The transparent cornea 31 is located at the front of the eye 30. The cornea 31 merges into a generally spheroid hard outer coat called the sclera 32. The muscles of ciliary body 33 serve to focus lens 34 and also secrete aqueous humor, which is a thin, transparent fluid within the eye 30. The aqueous humor fills the posterior chamber 36, and thereafter passes through the pupil 38 into the anterior chamber 40, and thereafter drains out of the eye into the Canal of Schlemm 42, where it is revascularized into the body.

Figure 3:
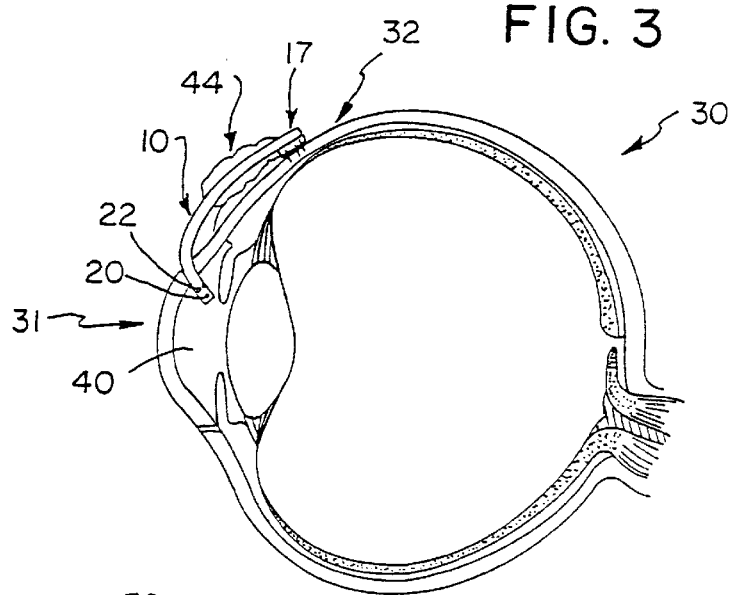
FIG. 3 is a sectional view of an eye, illustrating a glaucoma shunt of the present invention emerging from the anterior chamber of the eye to posterior globe wherein it is attached via an episcleral plate, surrounded by a fibrous capsule.

With reference to FIG. 3, the glaucoma shunt 10 is implanted using known ophthalmological procedures wherein a perforation is made in the sclera 32, extending into the anterior chamber 40. The perforation is made using any number of procedures known in the art, including such techniques as direct laser sclerostomy (i.e. using a holmium laser), trephine (using an Elliot trephine) or direct incision using a keratome or needle. The first sealed end 14 of tubular member 12 is then inserted into the perforation so that it extends into the anterior chamber 40. Open second end 16 and plate 17 is placed adjacent to a posterior position of the sclera of the eye 30. The flanges 18 of plate 17 are sutured directly to the sclera 32 of the eye 30 using perforations 19 for secure placement of the shunt 10 during the procedure. By securing the second end firmly in place, the first end is held firmly in place within the eye.

The tubular member 12 is a conduit for directing excess aqueous humor from the anterior chamber 40 through the perforations 20 and 22 into tubular member 12 for reabsorption into the vascular system through the fibrous capsule (bleb) 44 which forms around the shunt 10 after implantation. At the time of implantation, the shunt 10 may be sealed, allowing no aqueous humor to flow from the device. Alternatively, the shunt 10 may have at least one perforation 20 at the time of implantation, but any such perforation(s) would allow only a limited flow of aqueous humor through the device so as to prevent collapse of the eye 30 from excess loss of aqueous humor. The initial perforation(s) 20 may be located at any point along the portion of the wall of the tubular member 12 that is located within the anterior chamber 40 of the eye 30. The initial perforation(s) in the shunt are also of insufficient size to treat the glaucomatous eye, and additional perforations 22 are required to be created after implantation for proper functioning of the shunt 10 in relieving excess pressure. All perforations 20 and 22 must be located within the segment of the wall of tubular member 12 situated within anterior chamber 40 of the eye 30.

Stated in pressure terms, a glaucoma condition is defined by an anterior chamber pressure of at least 21 mm Hg above ambient, while in a normal eye, such pressure is in the range of 10–20 mm Hg. But a glaucomatous condition can create an intraocular pressure much greater than the 21 mm Hg threshold, frequently rising to 25–30 mm Hg, and in severe cases, rising to a level of 40–50 mm Hg. It is this high pressure that requires careful release of the excess aqueous humor. If care is not taken to release the pressure slowly, a severe drop in pressure can occur, to as low as 0–2 mm of Hg, which results in anterior chamber collapse, and possible permanent damage to the eye. By preventing any initial flow of aqueous humor through the shunt after implantation, or by providing an insubstantial level of flow so as to not greatly affect the intraocular pressure, the present invention allows the eye to be protected from such mishaps. In the present invention, the post-implantation flow rate of aqueous humor can be adjusted incrementally in a linear fashion, thus allowing close and careful monitoring of intraocular pressure levels to be maintained, allowing precise adjustment of flow rate of aqueous humor to be made, and preventing a rapid decrease in intraocular pressure from occurring. The shunt of the present invention allows the physician to adjust the flow rate of aqueous humor through the device as required on a low-risk, low cost out-patient basis.

Typically within about two weeks after implantation, a bleb 44 will form sufficiently around the implanted device. The individual physician will determine for each patient when the bleb 44 has sufficiently formed and the eye has recovered to an adequate degree to permit the flow of aqueous humor from the eye to begin, or be increased if initial perforations 20 were present in the shunt at the time of implantation. After formation of the bleb 44, the wall of tubular member 12 is punctured in a portion which is located within the anterior chamber 40 of the eye 30 by appropriate means, preferably by a laser as previously described, to create additional perforations 22 in at least one location so as to allow sufficient aqueous humor to drain from the anterior chamber 40 of the eye 30, through the shunt 10, and out into the bleb and thereafter to the vascular system for reabsorption. The laser beam is directed through the cornea 31, at the tubular member 12, and additional perforations 22 are created therein to allow a sufficient amount of aqueous humor to drain out through the shunt 10 to allow a decrease in intraocular pressure sufficient to treat the glaucomatous condition (i.e., to prevent additional damage to the eye due to the high intraocular pressure of aqueous humor due to that condition.) The shunt 10 affords the physician a simple and straightforward way to retain a high degree of control over the flow rate of aqueous humor, even after implantation. The rate of flow through the device, and, therefore, intraocular pressure of aqueous humor, may be adjusted by altering the number and size of perforations made in the wall of the tubular member 12. The rate of flow may be adjusted at intervals to ensure the proper rate of flow, for example, if intraocular pressure increases unacceptably, for any reason, due to advancement of the disease, as determined by the physician.

The shunt 10 has the further advantage of allowing drainage of aqueous humor from a number of openings along the wall of the tubular member 12. Therefore, if one or more openings become obstructed, the physician may correct the flow rate of aqueous humor by making additional openings in the tubular member 12. Additional perforations are made by simply directing a laser beam through the cornea and anterior chamber so that the laser beam strikes the wall of tubular member 12, creating additional perforations 22. The instrument used to make the perforations therefore does not directly contact the patient, and thus no further invasive procedure is required.

Figure 4:
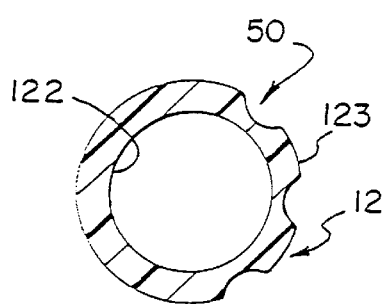
FIG. 4 is an enlarged cross-sectional view of the glaucoma shunt shown in FIG. 1, illustrating the preformed depression in the wall of the tubular member of the shunt.

As shown in FIG. 4, the tubular member 12 may optionally have several preformed depressions 50 at various points along its length. The depressions 50 are places within the wall of tubular member 12 such that the wall at the depressions 50 is thinner than at the remainder of the wall. By having portions of lesser thickness in the wall of tubular member 12, perforations 22 may be created after implantation through the depressions 50 by a laser utilizing less energy or operating at lower power than would be required if the laser beam was required to perforate the wall with the ordinary thickness away from the depression. These depressions may also be in the form of grooves placed about the circumference of tubular member 12. Since the laser is preferably directed through the cornea of the eye to the tubular member, it is in the best interest of the patient if the duration, power and delivered energy of the laser beam are kept to a minimum.

Figure 5:
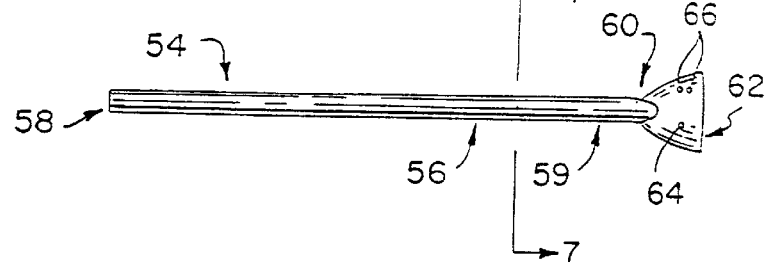
FIG. 5 is a top plain view of an alternative embodiment of a glaucoma shunt embodying the present invention, where the shunt comprises a reservoir.

An alternative embodiment 54 of the glaucoma shunt of the invention is shown in FIG. 5. Except for the differences hereinafter described, shunt 54 is formed of identical materials and implanted and perforated as described in connection with shunt 10.

Figure 7:
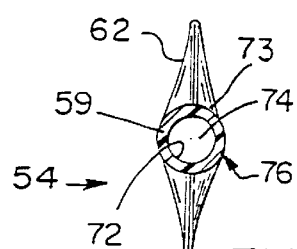
FIG. 7 is a view of a shunt 54 of the invention viewed from the first end 58 toward second end 60 when tubular member 56 is fully extended.

The shunt 54 is comprised of a tubular member 56 which, like tubular member 12 of apparatus 10, is a hollow tube having a first end 58, which is open, and a second open end 60, a wall 59 joining first end 58 and second end 60 and having, as shown in FIG. 7, an outside surface 73, and an inside surface 72. Inside surface 72 defines a space through which aqueous humor passes into a collection sac or reservoir 62. Second end 60 is open and inside reservoir 62. Collection sac in reservoir 62 has, as shown in FIG. 7, a wall 76, which has an outside surface and an inside surface (only outside surface shown in FIGS. 5 and 7). The inside surface defines the reservoir volume, into which tubular member projects somewhat such that end 60 is within the volume entirely contained and sealed within reservoir 62. The reservoir 62 is sealed to the tubular member 54 at a point proximate to second end 60. The reservoir 62 is approximately 100–500 mm$^2$ in size and may be a sack or pouch-like member, which is preferably made of silicone polymer, or other biologically inert material. These materials may be translucent, or pigmented. Pigmented materials assist in absorbing energy from the laser, allowing perforations to be made in the reservoir with less energy than would be required for a translucent silicone device. The reservoir 62 may be crescent-shaped, semi-circular, oval or round, and has thin, easily perforated walls.

Second end 60 of tube 56 is open and free of obstruction, and acts as a conduit for aqueous humor between the eye 30 and the reservoir 62. The second end 60 is sealed within the reservoir 62 by any suitable means well known in the art, with the preferred method being a silicone adhesive, preferably sealed during manufacture of the device.

The reservoir 62 may be sealed or may have at least one perforation 64 provided therein prior to implantation. If perforation(s) are provided prior to implantation, the perforations will be of small enough quantity or size so as to prevent a rapid decrease in intraocular pressure and damage to the eye upon implantation, as described above for shunt 10.

The reservoir 62 may be attached to the posterior of the eye 30 by any means commonly used in the art, preferably by being sutured directly to the sclera 32. Additional perforations 66 may be placed in the reservoir 62 periodically after implantation to effect a precise, linear adjustment of the flow rate of aqueous humor through the shunt 54. Perforations 66 are placed within the reservoir after the bleb has formed about shunt 54.

From the foregoing specification it can be appreciated that the glaucoma shunt device 10, and alternative embodiment 54, of the present invention can be quickly and easily implanted during a one-stage procedure, and firmly anchored in place by the physician. The shunt devices 10 and 54 prevent excess drainage of aqueous humor from the anterior chamber 40 of the eye 30, during the early post-operative period, allowing the bleb 44 to form around the implanted glaucoma shunt. After formation of the bleb 44, additional perforations are provided in the shunt device, of sufficient size and quantity to allow the flow of aqueous humor to be at a suitable rate to relieve the excess intraocular pressure within the eye 30 due to glaucoma. Periodic placement of these additional perforations allow the flow of aqueous humor through the shunt to be adjusted in a precise, linear fashion. Additional perforations may be added to the shunt devices 10 or 54 as needed at any time after implantation, in order to maintain the rate of removal of aqueous humor at an appropriate level.

I claim:

1. An adjustable flow rate implant shunt device for draining aqueous humor from an eye, comprising:
   a hollow tubular member having a first end and a second end, the first end being sealed and the second end being open, the tubular member having a size and shape to allow one of the ends to be inserted into an anterior portion of an eye and wherein the shunt device is sealed, allowing no aqueous-humor to flow from the device after insertion into the eye, and an episcleral plate, the plate being mounted adjacent to one of the ends.

2. The implant device of claim 1, wherein the device is made of a material selected from the group consisting of polymethylmethacrylate, polypropylene and silicone.

3. An adjustable flow rate implant shunt device for draining aqueous humor from an eye, comprising:
   a hollow tubular member having a first end and a second end, the first end being sealed and the second end being open, the tubular member having a size and shape to allow one of the ends to be inserted into an anterior portion of an eye and wherein the shunt device is sealed, allowing no aqueous humor to flow from the device after insertion into the eye, and an episcleral plate, the plate being mounted adjacent to one of the ends, wherein the device is capable of being perforated by a laser.

4. The implant device of claim 3, wherein the device is made of a material selected from the group consisting of polymethylmethacrylate, polypropylene and silicone.

* * * * *